(12) United States Patent
Glazier et al.

(10) Patent No.: US 9,402,606 B2
(45) Date of Patent: Aug. 2, 2016

(54) SNAP-ON VASCULAR CLOSURE DEVICE AND METHODS

(75) Inventors: Valerie J. Glazier, Eden Prairie, MN (US); Scott A. Kramer, Minneapolis, MN (US); Catherine A. Pipenhagen, Chanhassen, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 87 days.

(21) Appl. No.: 13/427,101

(22) Filed: Mar. 22, 2012

(65) Prior Publication Data

US 2012/0245624 A1  Sep. 27, 2012

Related U.S. Application Data

(60) Provisional application No. 61/466,775, filed on Mar. 23, 2011.

(51) Int. Cl.
*A61B 17/03* (2006.01)
*A61B 17/00* (2006.01)

(52) U.S. Cl.
CPC ... *A61B 17/0057* (2013.01); *A61B 2017/00601* (2013.01); *A61B 2017/00623* (2013.01); *A61B 2017/00654* (2013.01); *A61B 2017/00898* (2013.01)

(58) Field of Classification Search
CPC ............... A61B 17/0057; A61B 2017/00601; A61B 17/00623; A61B 17/00654; A61B 17/00898

USPC .................. 606/230, 213, 148, 232
See application file for complete search history.

(56) References Cited

U.S. PATENT DOCUMENTS

| 6,045,569 | A | 4/2000 | Kensey et al. |
|---|---|---|---|
| 6,090,130 | A | 7/2000 | Nash et al. |
| 6,699,261 | B1 * | 3/2004 | Cates et al. .................. 606/213 |
| 7,931,670 | B2 * | 4/2011 | Fiehler et al. ................ 606/213 |
| 8,317,824 | B2 * | 11/2012 | Jenson et al. ................ 606/213 |
| 2006/0265006 | A1 * | 11/2006 | White et al. .................. 606/232 |
| 2007/0005081 | A1 * | 1/2007 | Findlay et al. ............... 606/148 |
| 2008/0221615 | A1 * | 9/2008 | Ginn et al. .................... 606/213 |
| 2010/0217311 | A1 * | 8/2010 | Jenson ............... A61B 17/0057 606/213 |
| 2010/0292532 | A1 * | 11/2010 | Kadykowski et al. ........ 600/104 |

* cited by examiner

*Primary Examiner* — Julie A Szpira
(74) *Attorney, Agent, or Firm* — Holland & Hart

(57) ABSTRACT

A tissue puncture closure assembly including a wire assembly and a sealing pad delivery device. The wire assembly includes a proximal end portion, a distal end portion, and a temporary expandable anchor positioned at the distal end portion. The sealing pad delivery device includes a carrier tube, a sealing pad positioned in the carrier tube, and a lateral wire slot. The lateral wire slot is defined in an outer surface of the sealing pad delivery device and extends along at least a portion of a length of the sealing pad delivery device. The lateral wire slot is configured to permit mounting of the sealing pad delivery device to the wire assembly in a lateral direction.

12 Claims, 12 Drawing Sheets

SNAP-ON VASCULAR CLOSURE DEVICE AND METHODS

CROSS-REFERENCE TO RELATED APPLICATION

This application claims the benefit of the filing date of U.S. Provisional Application No. 61/466,775, filed 23 Mar. 2011, and entitled SNAP-ON VASCULAR CLOSURE DEVICE AND METHODS, the disclosure of which is hereby incorporated in its entirety by this reference.

TECHNICAL FIELD

The present disclosure relates generally to medical devices and more particularly to vascular closure devices.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., a catheter) may pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, may be stopped by utilizing vascular closure devices, such as those described in U.S. Pat. Nos. 6,090,130 and 6,045,569, which are hereby incorporated in their entireties by this reference.

Typical closure devices such as the ones described in the above-mentioned patents place a sealing plug at the tissue puncture site. Deployment of the sealing plug may involve ejecting the sealing plug from within the closure device sheath to a location in alignment with and adjacent to the tissue puncture along an outer surface of the vessel and within a percutaneous tissue tract. Mounting the closure device onto a proximal end of the guidewire and advancing the closure device to the tissue puncture site may require both of the operator's hands. However, in at least some treatment procedures, one of the operator's hands is used to apply and maintain pressure to the patient adjacent to the tissue puncture to provide hemostasis and hold the guidewire within the vessel. Releasing the operator's hand from applying pressure to the patient may result in complications in the procedure. Opportunities exist for improvements in this technical area.

SUMMARY

One aspect of the present disclosure relates to a tissue puncture closure assembly that includes a wire assembly and a sealing pad delivery device. The wire assembly includes a proximal end portion, a distal end portion, and a temporary expandable anchor positioned at the distal end portion. The sealing pad delivery device includes a carrier tube, a sealing pad positioned in the carrier tube, and a lateral wire slot. The lateral wire slot is defined in an outer surface of the sealing pad delivery device and extends along at least a portion of a length of the sealing pad delivery device. The lateral wire slot is configured to permit mounting of the sealing pad delivery device to the wire assembly in a lateral direction.

The lateral wire slot may be configured to provide a snap-fit connection of the sealing pad delivery device to the wire assembly. The sealing pad delivery device may further include a housing, and the lateral wire slot is formed in outer surfaces of the housing, the carrier tube, and the sealing pad. The wire assembly may further include a handle positioned at the proximal end portion and an anchor actuator mounted to the handle. The wire assembly may include a tubular portion having a lumen and a wire member positioned in the lumen, wherein relative movement between the tubular portion and the wire member expands and contracts the anchor. The wire assembly may further include an anchor actuator positioned at the proximal end portion and configured to move the wire member relative to the tubular portion. The sealing pad delivery device may include a wire lumen sized to receive a portion of the wire assembly that is located between the distal and proximal end portions, and the proximal end portion of the wire assembly is sized greater than the wire lumen.

Another aspect of the present disclosure relates to a tissue puncture closure device adapted for insertion into and sealing of a tissue puncture in a tissue wall. The device includes a housing, a carrier tube extending from the housing, a sealing pad positioned in the carrier tube, a guidewire lumen, and a lateral guidewire slot. The guidewire lumen extends through the housing and carrier tube. The lateral guidewire slot is open from an outer side surface of the closure device into the guidewire lumen. The closure device is operable to mount to a guidewire that is positioned in the tissue puncture by inserting the guidewire through the lateral guidewire slot and into the guidewire lumen.

A portion of the guidewire located between proximal and distal ends of the guidewire may be inserted into the lateral guidewire slot. The sealing pad may include a slot feature arranged in alignment with the lateral guidewire slot. The closure device may further include a wire locking member operable to resist axial movement of the closure device relative to the guidewire. The closure device may also include a tube retractor actuator that is operable to withdraw the carrier tube relative to the housing to expose the sealing pad. The lateral guidewire slot may include a tapered construction. The lateral guidewire slot may be configured to provide a snap-fit connection between the guidewire and the closure device.

Another aspect of the present disclosure relates to a method of sealing a tissue puncture in an internal tissue wall that is accessible through a percutaneous incision. The method may include providing a closure device and a guidewire, the closure device including a sealing pad and a lateral guidewire slot, and the guidewire including distal and proximal ends. The method may also include advancing a distal end of the guidewire through the percutaneous incision and the tissue puncture, and mounting the closure device to the guidewire by inserting a portion of the guidewire spaced between the distal and proximal ends of the guidewire through the lateral guidewire slot.

Mounting the closure device may include arranging the closure device laterally adjacent to the guidewire with the lateral guidewire slot aligned facing the guidewire, and moving the closure device in a lateral direction toward the guidewire. The guidewire may include a handle positioned at a location proximal of the percutaneous incision when the distal end of the guidewire is advanced through the percutaneous incision and the tissue puncture, and mounting the closure device to the guidewire includes mounting the closure device to the guidewire at a location distal of the handle. The lateral guidewire slot may be defined at least in part by the sealing pad, and mounting the closure device to the guidewire includes inserting the guidewire into the sealing pad. The method may also include operating the closure device to expose the sealing pad in the percutaneous incision and withdrawing the guidewire through the exposed sealing pad. The closure device may include a carrier tube and a housing, the lateral guidewire slot being defined in the carrier tube and housing, and mounting the closure device to the guidewire includes inserting the guidewire into the carrier tube and housing.

Additional advantages and novel features will be set forth in the description which follows or may be learned by those skilled in the art through reading these materials or practicing the examples disclosed herein.

BRIEF DESCRIPTION OF THE DRAWINGS

The accompanying drawings illustrate various embodiments of the present disclosure and are a part of the specification. The illustrated embodiments are merely examples and are not intended to be limiting.

FIG. 3A is a cross-sectional view of the closure device of FIG. 3 taken along cross-section indicators 3A-3A.

FIG. 4A is a cross-sectional view of the guidewire shown in FIG. 4 taken along cross-section indicators 4A-4A.

Throughout the drawings, identical reference numbers designate similar, but not necessarily identical, elements.

DETAILED DESCRIPTION

As mentioned above, vascular procedures are conducted throughout the world and require access to a vessel through a puncture. Often, the vessel is a femoral artery. To close the puncture following completion of the procedure, a closure device may be used to position a sealing pad within a percutaneous incision adjacent to the puncture. The closure device may be advanced over a guidewire that is positioned extending through the percutaneous incision and the puncture. The guidewire may include a temporary anchor feature that is expandable within the vessel to provide an anchoring, locating and/or sealing function internal to the vessel, and returns to an unexpanded state for removal of the guidewire through the percutaneous incision and puncture after the sealing plug has been positioned in the percutaneous incision.

Advancing the closure device over the guidewire to the percutaneous incision typically involves inserting a proximal end of the guidewire into a distal opening of the dilator and closure device at a location that is spaced relatively far from the percutaneous incision. Because of the relatively flexible nature of the guidewire and the distance from the percutaneous incision to the proximal end of the guidewire, both of the operator's hands are usually needed to mount the closure device to the guidewire and withdraw the dilator and closure device from off the proximal end of the guidewire. If both of the operator's hands are needed to mount the closure device to the guidewire, it may be difficult for the operator to perform other aspects of the patient treatment such as applying pressure to the patient adjacent to the percutaneous incision to create hemostasis and/or retain a distal end of the guidewire in the puncture.

Some guidewires include a temporary expandable anchor that is positioned near a distal end of the guidewire. The anchor may have a collapsed state or position that permits passing of the anchor and distal end of the guidewire through the incision and puncture (i.e., into a vessel lumen). The guidewire may include actuator features positioned outside of the patient that are operable to move the anchor into an expanded state or position. A size of the anchor when in the expanded state limits withdrawal of the anchor out of the puncture. The anchor may provide a sealing and anchoring function when in the expanded state. The actuator features of the guidewire are typically sized small enough that the closure device may be advanced over the proximal end of the guidewire with the actuator features passing through an interior of the closure device. Actuator features of this relatively small size may be difficult for the operator to handle such as when the operator moves the actuator features to expand and collapse the anchor during treatment of the patient.

Figure 1:
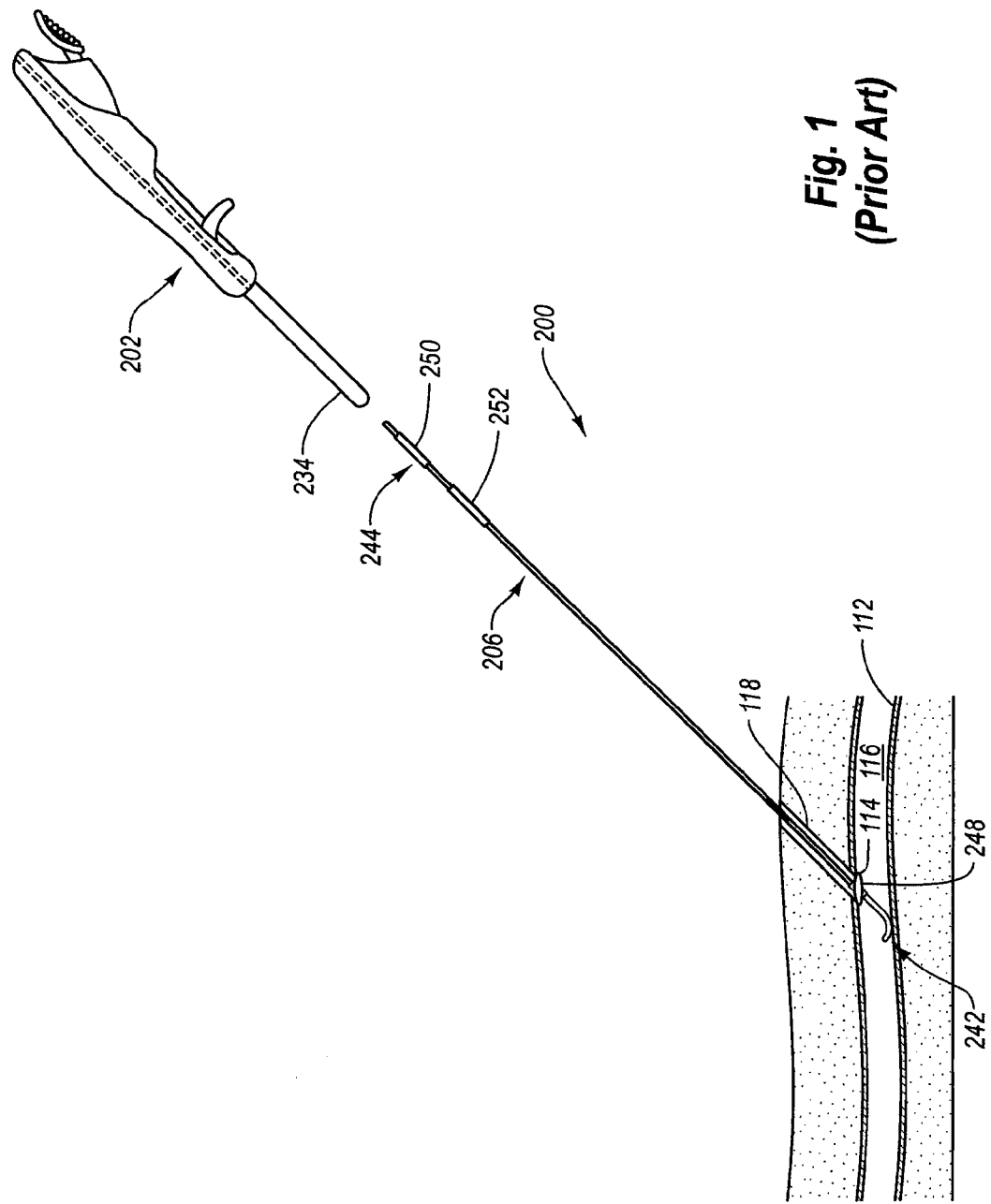
FIG. 1 is a side view of an example closure device in the prior art being mounted to a guidewire by inserting a proximal end of the guidewire to a distal end of the closure device.
Figure 2:
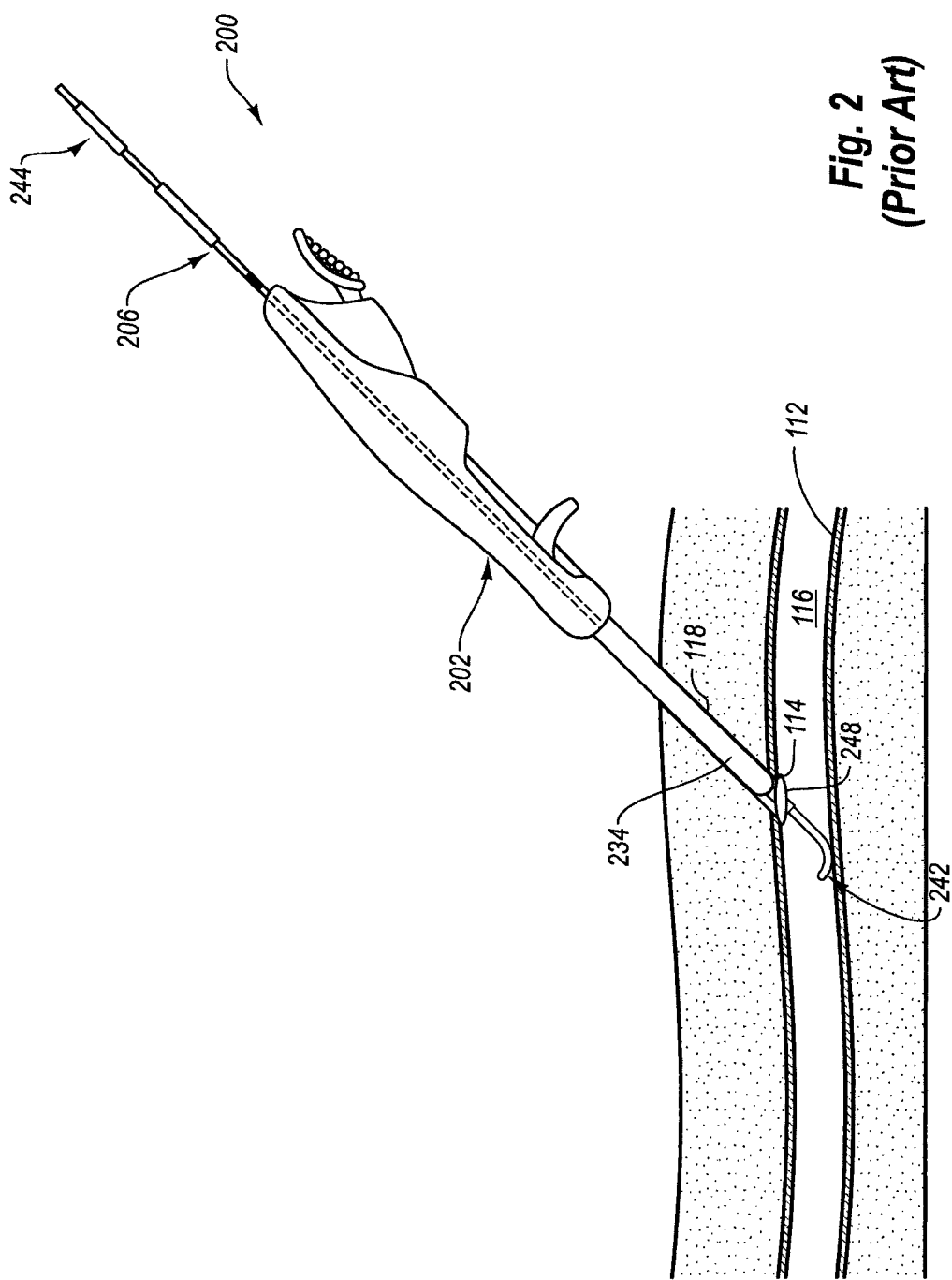
FIG. 2 is a side view of the closure device of FIG. 1 advanced into a percutaneous incision.

Referring to FIGS. 1 and 2, an example tissue puncture treatment assembly 200 that involves advancing a closure device 202 (also referred to herein as a sealing pad delivery device) over a guidewire 206 (also referred to herein as a locator wire assembly) is shown and described. The guidewire 206 has a distal end portion 242 that is inserted through a percutaneous incision 118 and a vessel puncture 114 (also referred to herein as a tissue puncture) until a temporary anchor 248 of the guidewire is positioned in a vessel interior 116 at a location distal of the vessel puncture 114. A pair of actuator features 250, 252 at a proximal end portion 244 of the guidewire may be operated to expand the anchor 248 into the expanded state shown in FIGS. 1 and 2.

The closure device 202 is shown in FIG. 1 positioned proximal of the proximal end portion 244 of the guidewire 206. Mounting the closure device 202 to the guidewire 206 includes inserting the proximal end portion 244 (including the actuator features 250, 252) into an open distal end 234 of the closure device 202. The closure device 202 is advanced along the guidewire 206 until the open distal end 234 of the carrier tube is inserted into the percutaneous incision 118. The closure device 202 may then be operated to deploy a sealing pad (not shown in the figures) within the percutaneous incision 118 at a location adjacent to the vessel puncture 114.

Typically, the actuator features 250, 252 are sized small enough to pass through the open distal end 234 of the closure device 202 and the sealing pad (not shown in FIG. 1) carried in the closure device 202. Operating actuator features 250, 252 of this relatively small size to expand and/or contract the anchor 248 may be difficult for the operator to conduct with the precision and accuracy needed.

The devices and methods of the present disclosure may provide the operator with the ability to advance and withdraw the closure device over the guidewire using one hand as part of treating the patient. The operator's other hand may be used to maintain pressure on the patient adjacent the tissue tract, for example, to limit blood flow through a vessel of the patient being treated or to hold a distal end of the guidewire within the vessel being treated.

Further, the devices and methods disclosed herein may provide anchor actuator features of increased size that may be easier for the operator to handle when expanding and contracting the anchor.

In at least one example, the closure device is configured to mount to the guidewire in a lateral direction rather than solely in an axial direction. Such lateral mounting of the closure device may make it possible to mount the closure device to the guidewire at a location distal of the anchor actuator features so that the anchor actuator features do not have to pass through interiors of the closure device and sealing pad. In at least one arrangement, the anchor actuator features may include a handle portion that has improved ergonomics and an actuator feature that moves relative to the housing that has improves ease of use for the operator.

While the vascular instruments shown in the attached figures and described below may include procedural sheaths and puncture sealing devices, the application of principles described herein are not limited to the specific devices shown. The principles described herein may be used with any medical device. Therefore, while the description below is directed primarily to vascular procedures and certain embodiments of a vascular closure device, the methods and apparatus are only limited by the appended claims. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

As used in this specification and the appended claims, the term "compact" or "compacting" is used broadly to mean any type of tamping (i.e., packing down by one or a succession of blows or taps or smooth, steady pressure, but not by excessive force), compacting, or compressing. The term "engage" and "engageable" are also used broadly to mean interlock, mesh, or contact between two devices. Likewise "disengage" or "disengageable" means to remove or capable of being removed from interlock, mesh, or contact. A "tube" is an elongated device with a passageway. The passageway may be enclosed or open (e.g., a trough). A "lumen" refers to any open space or cavity in a device or bodily organ, especially in a blood vessel. The words "including" and "having," as used in the specification, including the claims, have the same meaning as the word "comprising."

Referring now to FIGS. 3-12, an example tissue puncture treatment assembly 100 (see FIGS. 5-10) is shown and described. The tissue puncture treatment assembly 100 includes a sealing pad delivery device 102 (also referred to herein as a "closure device 102"), and locator wire assembly 106 (also referred to herein as a "guidewire 106"). The sealing pad delivery device 102 is configured to deliver a sealing pad to a tissue puncture. In at least one example, the sealing pad delivery device 102 delivers a sealing pad to a position adjacent to and proximal of a vessel puncture and within a percutaneous incision. The locator wire assembly 106 is typically pre-positioned extending through the tissue puncture and used as a guiding device over which the sealing pad delivery device 102 may be advanced into position adjacent to the tissue puncture.

Figure 3:
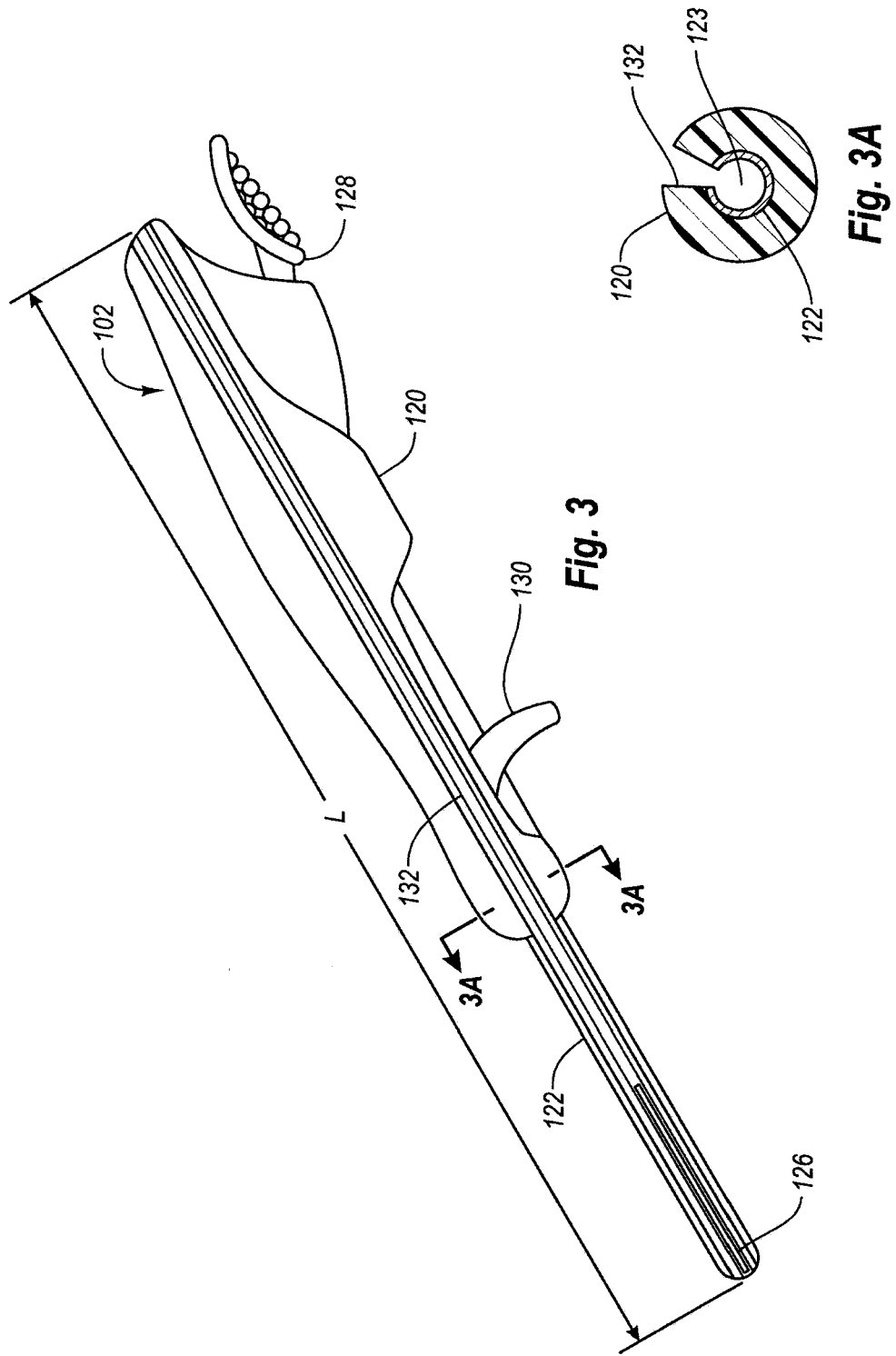
FIG. 3 is a side view of an example closure device in accordance with principles of the present disclosure.

FIG. 3 illustrates the sealing pad delivery device 102 in a close up side view. The sealing pad delivery device 102 includes a housing 120, a carrier tube 122 extending within and distally from the housing 120 (e.g., see FIG. 3A), and a sealing pad 126 positioned in the carrier tube 122. The sealing pad delivery device 102 may also include a wire locking member 128 that is configured to releasably lock the sealing pad delivery device 102 to the guidewire 106, and a tube retractor actuator 130 that moves the carrier tube 122 relative to the housing 120 (e.g., into handle 120) to expose the sealing pad 126 outside of the sealing pad delivery device 102. Other types of devices may be used in place of or in combination with the wire locking member 128 and the retractor actuator 130 to limit relative axial movement between the guidewire 106 and sealing pad delivery device 102 and dispose the sealing pad 126 adjacent to the tissue puncture.

The sealing pad delivery device 102 may further include a lateral wire lumen slot 132. The lateral wire lumen slot 132 may be configured for insertion of the guidewire into the sealing pad delivery device 102 in a lateral or radial direction rather than insertion through an open end in an axial direction as described above with reference to the embodiment of FIGS. 1 and 2. The lateral wire lumen slot 132 may extend along substantially the entire length L of the sealing pad delivery device 102. In other arrangements, the lateral wire lumen slot 132 extends along only a portion of the length L, such as long only the carrier tube 122. The lateral wire lumen slot 132 may be defined in part by both the housing 120 and the carrier tube 122. In some arrangements, the sealing pad 126 also includes a wire lumen 134 and a lateral slot opening 136 (see FIG. 8). Typically, the lateral slot opening 136 of the sealing pad 126 is radially aligned with the lateral wire lumen slot 132 such that insertion of the guidewire 106 into the lateral wire lumen slot 132 results in positioning of the guidewire 106 within the wire lumen 134 of the sealing pad 126.

Once the locator wire assembly 106 is inserted through the lateral wire lumen slot 132 and into wire lumen 123 of the sealing pad delivery device 102 (see FIG. 3A), the sealing pad delivery device 102 may be advanced and withdrawn axially relative to the locator wire assembly 106 as will be described in further detail below.

The lateral wire lumen slot 132 may be configured with a tapered or sloped opening as shown in FIG. 3A. The tapered construction of the lateral wire lumen slot 132 may be helpful in initially locating the locator wire assembly 106 within the lateral wire lumen slot 132 as the locator wire assembly 106 is moved laterally into the wire lumen 123.

The construction of the lateral wire lumen slot 132 in combination with, for example, the cross-sectional shape, material composition, and other physical properties of the sealing pad delivery device 102 may influence the ease or difficulty of inserting the locator wire assembly 106 into the wire lumen 123 in the lateral direction. For example, the generally tapered construction of the lateral wire lumen slot 132 shown in FIG. 3 in combination with a material composition that provides flexibility for the sealing pad delivery device 102 may result in some spreading open of the lateral wire lumen slot 132 as the locator wire assembly 106 is inserted, followed by return back to the original shape once the locator wire assembly 106 is positioned within the wire lumen 123.

In some arrangements, the sealing pad delivery device 102 provides a snap-fit interface between the sealing pad delivery device 102 and the locator wire assembly 106 as the locator wire assembly 106 is moved through the lateral wire lumen slot 132 and into the wire lumen 123. In other arrangements, the sealing pad delivery device 102 may be constructed to provide one-way insertion of the locator wire assembly 106 through the lateral wire lumen slot 132. For example, the locator wire assembly 106 may move through the lateral wire lumen slot 132 in the radial inward direction, but is restricted from moving back through the lateral wire lumen slot 132 in the radial outward direction.

In at least some methods of use, the sealing pad delivery device 102 may be mounted to the locator wire assembly 106 in a lateral direction in a step prior to disposing the sealing pad adjacent to the tissue puncture, followed by axial withdrawal of the locator wire assembly 106 out of the sealing pad delivery device 102 after the sealing pad has been disposed adjacent to the tissue puncture. In such a method, one-way insertion of the locator wire assembly 106 through the lateral wire lumen slot 132 into the wire lumen 123 may have advantages in helping retain the sealing pad delivery device 102 on the locator wire assembly 106 during treatment of the patient while still providing the lateral mounting described above.

Figure 4:
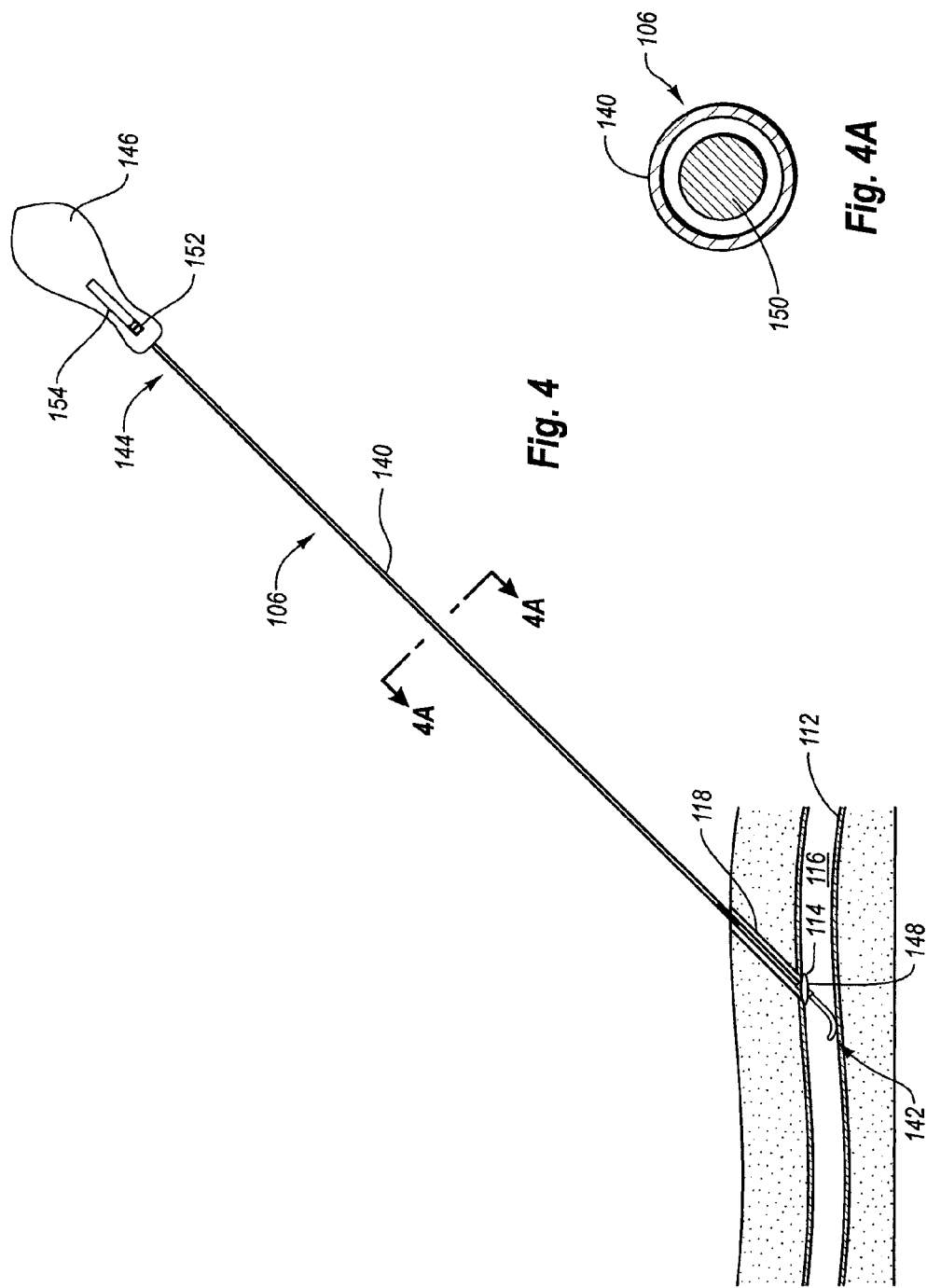
FIG. 4 is a side view of an example guidewire in accordance with principles of the present disclosure inserted through a tissue puncture and percutaneous incision.
Figure 12:
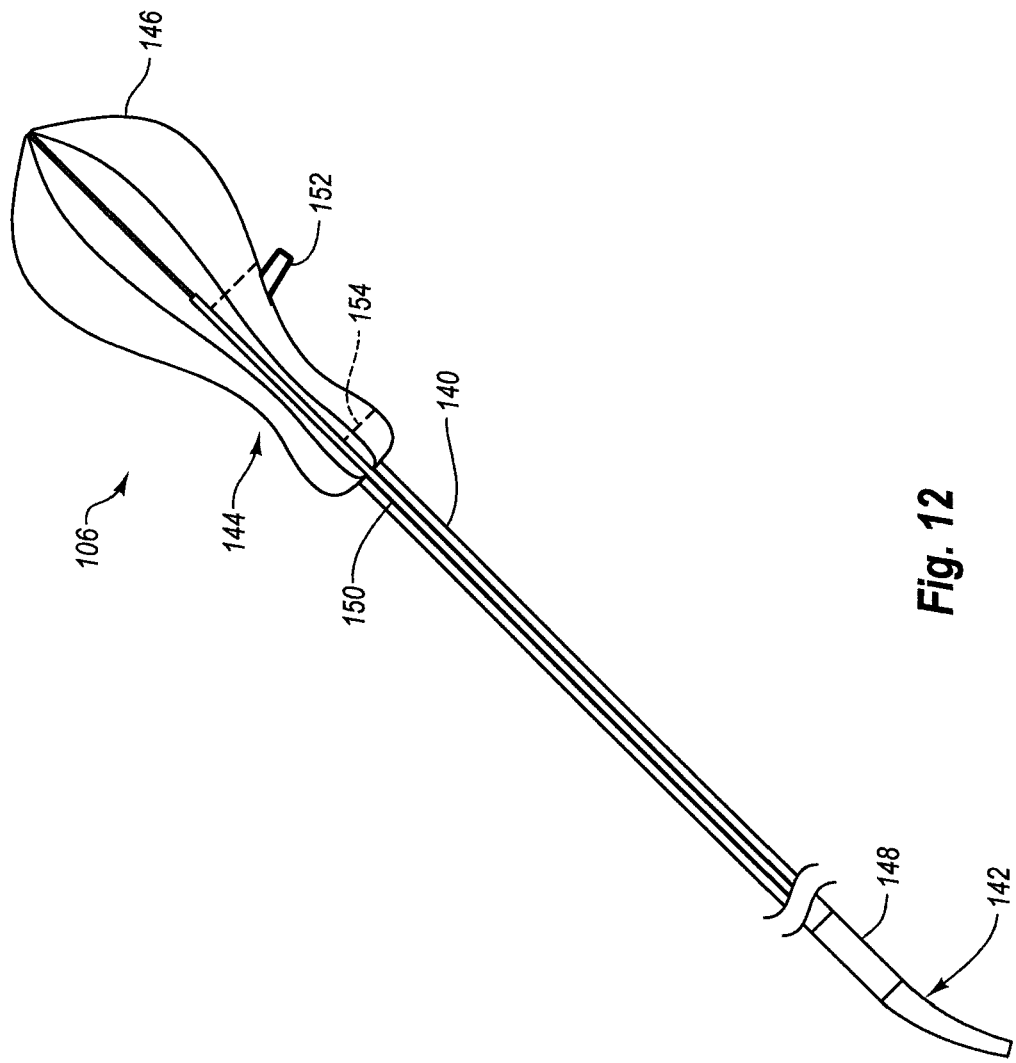
FIG. 12 is a partial cross-sectional view of a portion of the guidewire shown in FIG. 4.

Referring now to FIGS. 4, 4A and 12, the locator wire assembly 106 is described in further detail. The locator wire assembly 106 may include a locator tube 140, a distal end portion 142, a proximal end portion 144, a handle or housing 146, and a temporary anchor 148. The anchor 148 is typically positioned at the distal end portion 142. The anchor 148 is operable between a collapsed state or position (see FIGS. 9 and 10) that permits advancement of the distal end portion 142 through the percutaneous incision 118 and vessel puncture 114 into the vessel interior 116, and an expanded position (see FIG. 4) that restricts withdrawal in a proximal direction.

The locator wire assembly 106 may further include an anchor actuator wire 150 (see FIG. 4A) that extends from the anchor 148 proximally to the handle 146 at the distal end portion 144. A wire actuator 152 may be exposed at the proximal end portion 144 such as, for example, within an actuator slot 154 defined in the handle 146 (see cut out portion of FIG. 12). In at least one example, advancing the wire actuator 152 in the distal direction within the actuator slot 154 (a distal axial direction $A_2$) expands the anchor 148 into the expanded state shown in FIG. 4. Moving the wire actuator 152 within the actuator slot 154 in the proximal direction $A_1$ returns the anchor 148 to the collapsed state or position shown in FIGS. 9 and 10.

When the anchor 148 is in the expanded state shown in FIG. 4, the anchor 148 may provide hemostasis (i.e., stop blood flow through the vessel puncture 114). When in the expanded state shown in FIG. 4, the anchor 148 may also provide an anchor function for the sealing pad delivery device 102 when disposing the sealing pad adjacent to the vessel puncture 114. Providing an anchor within the vessel 112 while disposing of the sealing pad may improve alignment of the sealing pad relative to the vessel puncture 114, which may provide reduced leakage and an improved seal.

The handle 146 may be significantly larger in size than the actuator features 250, 252 described above with reference to guidewire 206. The increased size of handle 146, among other aspects such as, for example, the shape and material composition of handle 146, may provide an improved ease in use of locator wire assembly 106 as compared to the guidewire 206 described above. Other types of actuator arrangements besides the wire actuator 152, which is operable within an actuator slot 154, may be used to advance and withdraw the anchor actuator wire 150 relative to the locator tube 140. In other arrangements, the anchor 148 is operable between collapsed and expanded states by moving the wire actuator 152 within the actuator slot 154 in an opposite direction to that described above. In some examples, thumb or finger actuated devices including, for example, roller actuators, and in some cases electronic or powered devices, may be used to move the anchor between expanded and collapsed positions. In still further arrangements, the handle 146 and wire actuator 152 may be positioned along the locator tube 140 and anchor actuator wire 150 at locations distal of the proximal end of at least one of the locator tube 140 and anchor actuator wire 150.

The handle 146 and wire actuator 152 may have any shape or construction desired. The construction of handle 146 and wire actuator 152 is not limited to a size or shape that may be passed through the sealing pad delivery device 102, which is required of the guidewire 206 described above with reference to the tissue puncture treatment assembly 200.

Operation of the tissue puncture treatment assembly 100 is now described in more detail with reference to FIGS. 4-11. The locator wire assembly 106 is advanced through the percutaneous incision 118 and vessel puncture 114 until a distal end portion 142 (including anchor 148) is positioned within the vessel interior 116. The wire actuator 152 is advanced within the actuator slot 154 in the handle 146 to expand the anchor 148 into the expanded state shown in FIG. 4. The locator wire assembly 106 is then withdrawn proximally until the anchor 148 engages against the vessel wall adjacent to the vessel puncture 114.

The locator wire assembly 106 may be positioned within the vessel puncture 114 and percutaneous incision 118 using, for example, an introducer sheath or similar device. In some instances, the introducer sheath is a procedural sheath used for insertion of treatment or diagnostic instruments into the vessel interior 116 for treatment of the patient. In at least one example, the insertion sheath may include a feature similar to the lateral wire lumen slot 132 described above with reference to FIG. 3 to permit removal of the insertion sheath from the locator wire assembly 106 without the need for withdrawing the insertion sheath proximally over the handle 146 and other features at the proximal end portion 144 of the locator wire assembly 106.

Figure 5:
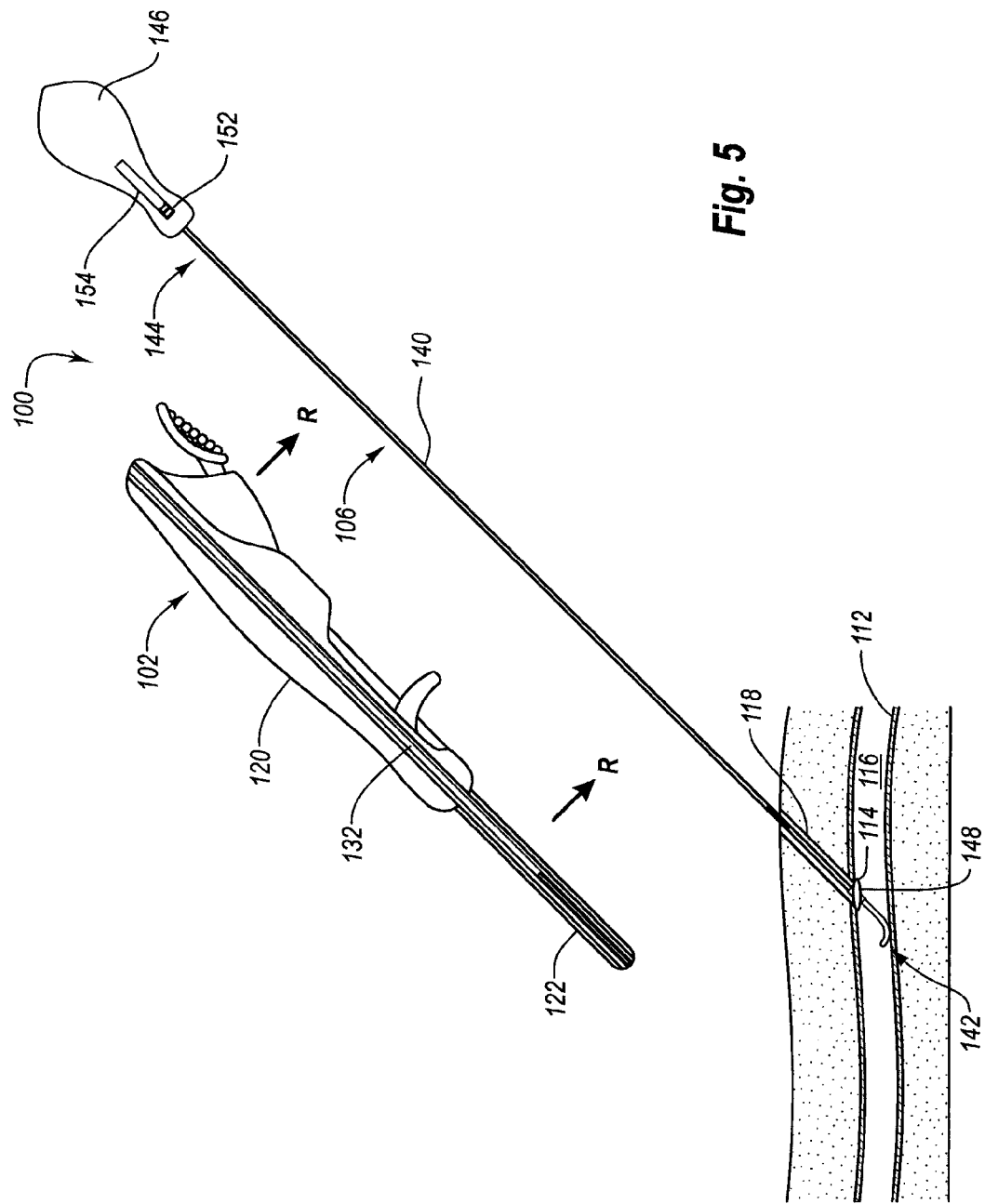
FIG. 5 is a side view of the closure device of FIG. 3 positioned laterally adjacent to the guidewire of FIG. 4.
Figure 6:
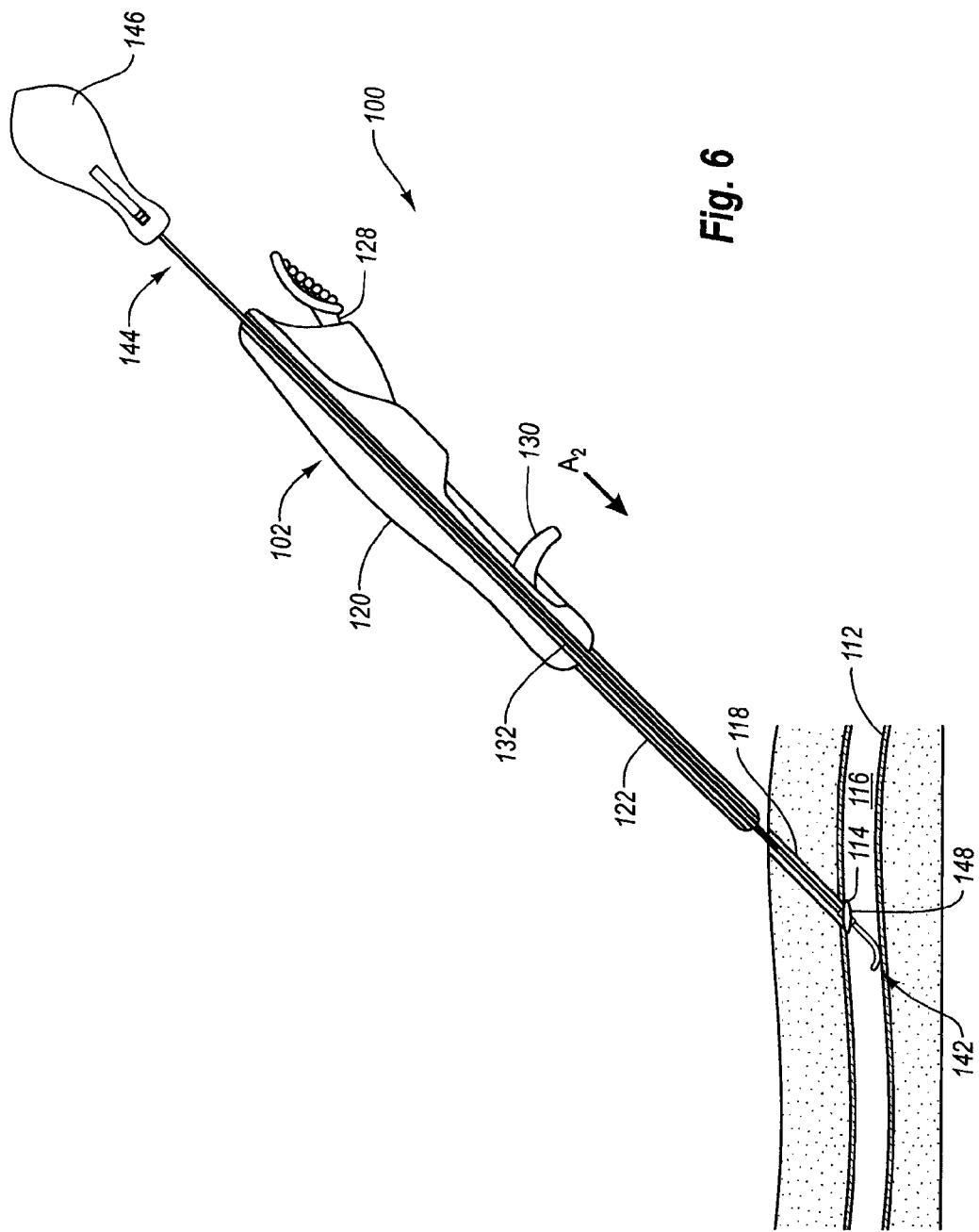
FIG. 6 is a side view of the closure device of FIG. 5 moved laterally to a mounted position on the guidewire of FIG. 5.

Once the locator wire assembly 106 is positioned with the anchor 148 contacting the vessel as shown in FIGS. 4 and 5, the sealing pad delivery device 102 may be moved into position laterally or radially adjacent to the locator wire assembly 106 as shown in FIG. 5. Typically, the sealing pad delivery device 102 is positioned adjacent to the locator wire assembly 106 at a location between the distal and proximal end portions 144, 142 of the locator wire assembly 106. The lateral wire lumen slot 132 may be arranged facing the locator wire assembly 106 so that moving the sealing pad delivery device 102 in the lateral or radial direction R inserts the locator wire assembly 106 through the lateral wire lumen slot 132 and into the sealing pad delivery device 102. As clearly shown in FIG. 5, a wire locking member 128 on the sealing pad delivery device 102 also moves laterally relative to the locator wire assembly 106 (see also FIG. 6) as the sealing pad delivery device 102 moves in the lateral or radial direction R and positions the wire assembly 106 in the wire lumen 123.

As described above, the sealing pad 126 may also include a lateral slot opening 136 that is aligned with the lateral wire lumen slot 132 so that inserting the locator wire assembly 106 laterally into the sealing pad delivery device 102 positions at least a portion of the locator wire assembly 106 within the wire lumen 134 of the sealing pad 126.

After the locator wire assembly 106 has been laterally inserted into the sealing pad delivery device 102 through the lateral wire lumen slot 132 (see FIG. 6), the sealing pad delivery device 102 may be advanced distally in the direction A₂ until at least a portion of the carrier tube 122 is positioned within the percutaneous incision 118.

Figure 7:
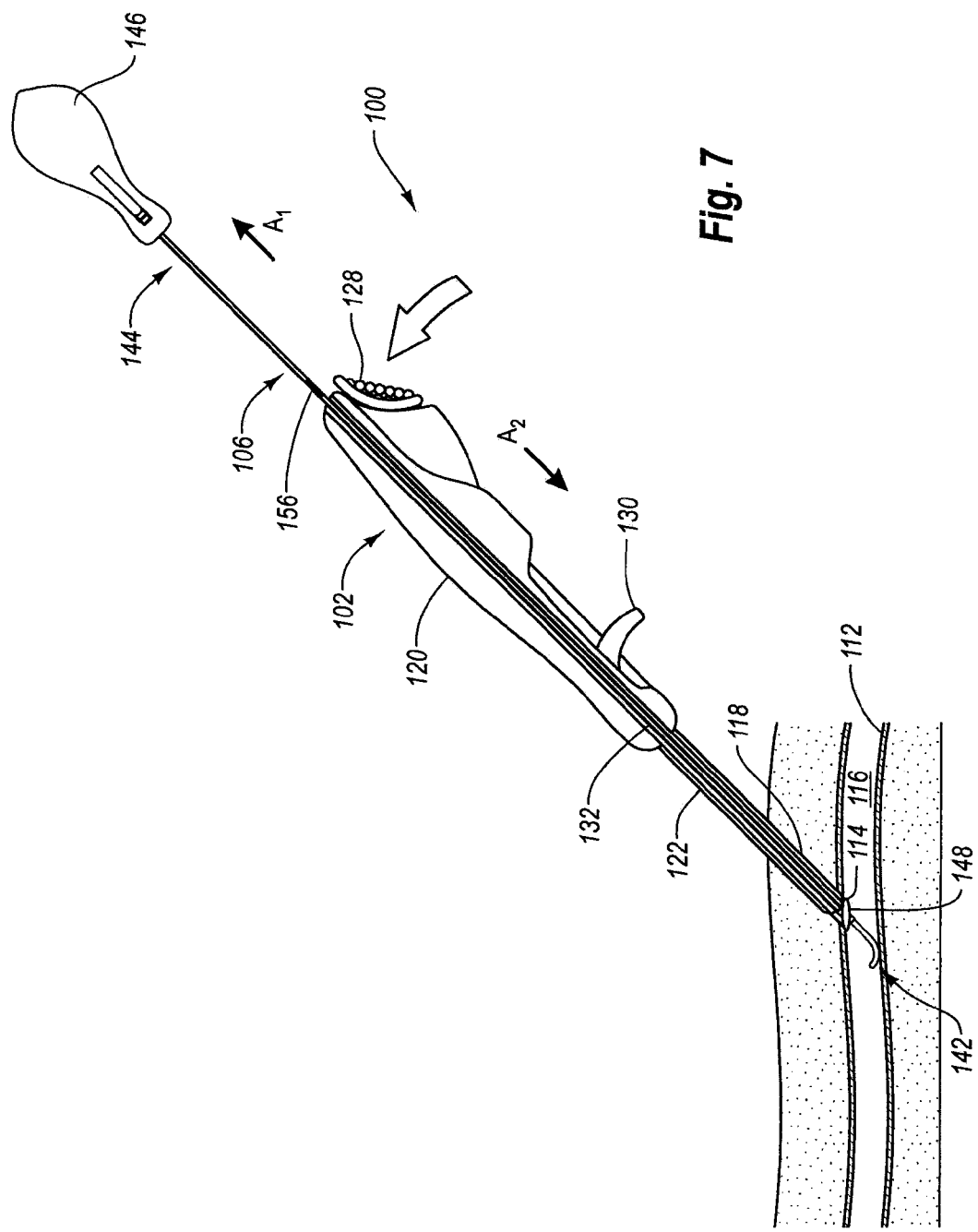
FIG. 7 is a side view of the closure device of FIG. 6 advanced over the guidewire and into the percutaneous incision.

Referring to FIG. 7, once the sealing pad delivery device 102 is arranged at a desired position relative to the vessel puncture 114 in the percutaneous incision 118 (i.e, as indicated by exposure of a marker 156 along the length of the locator wire assembly 106), the wire locking member 128 is actuated to fix or lock an axial position of the sealing pad delivery device 102 relative to the locator wire assembly 106. Other means of retaining the sealing pad delivery device 102 in a set or fixed axial position relative to the locator wire assembly 106 may be accomplished in place of or in combination with use of the wire locking member 128. In at least one example, a proximally directed axial force in the direction A₁ may be applied to the locator wire assembly 106 (i.e., at the handle 146) while applying a distally applied axial force in the direction A₂ to the sealing pad delivery device 102 at the time of actuating the wire locking member 128 for improved positioning of the sealing pad delivery device 102 adjacent to the vessel puncture 114.

Figure 8:
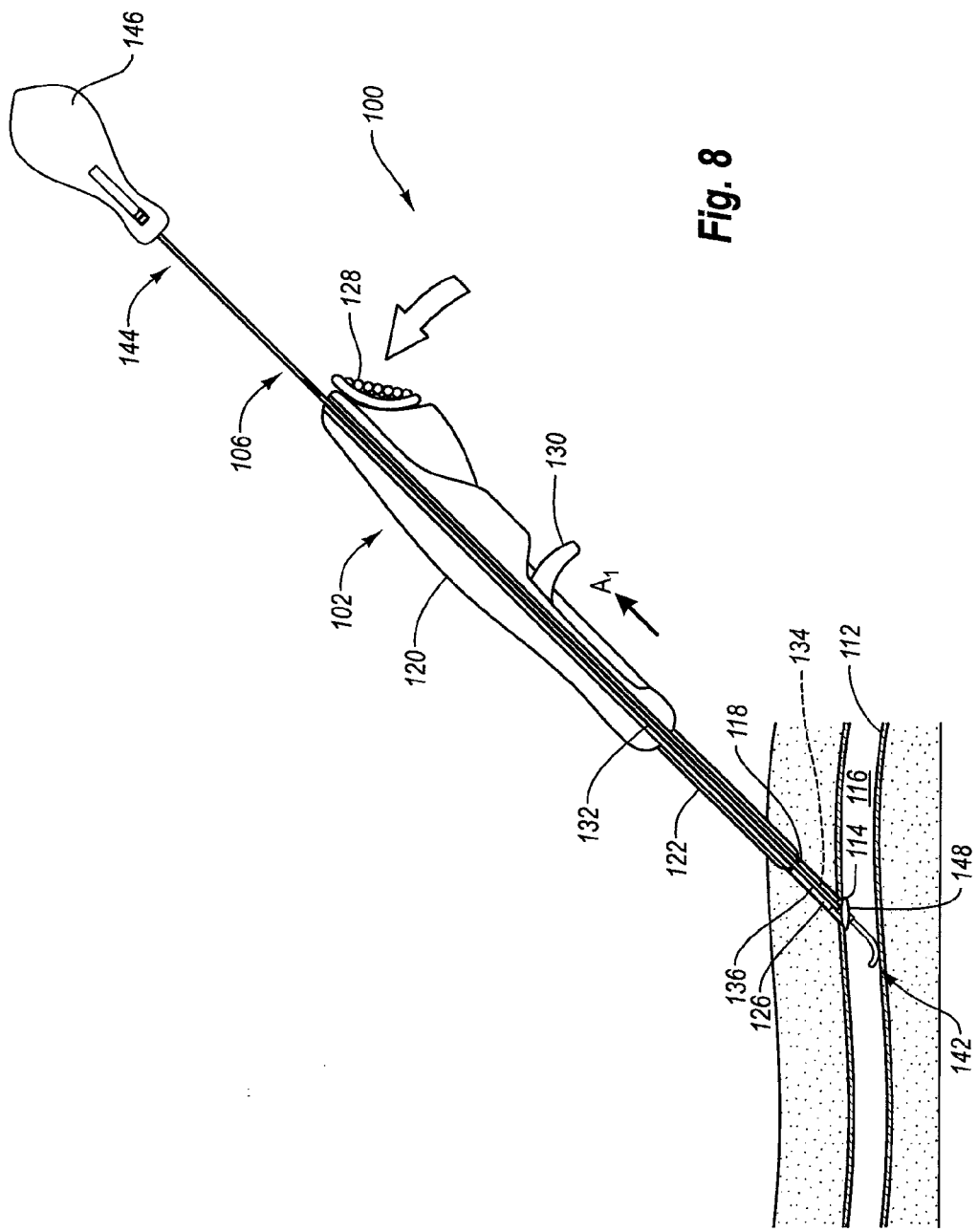
FIG. 8 is a side view of the closure device of FIG. 7 with the closure device operated to expose a sealing pad within the percutaneous incision.

Referring now to FIG. 8, the operator may actuate the tube retractor actuator 130 in the proximal direction A₁ to withdraw the carrier tube 122 in a proximal direction thereby exposing the sealing pad 126 within the percutaneous incision 118. Once the sealing pad 126 is exposed within the percutaneous incision 118, the sealing pad 126 may begin to absorb fluids (i.e., blood) and being to swell within the percutaneous incision 118 to seal the vessel puncture 114 and percutaneous incision 118. The sealing pad 126 may expand to close the lateral slot opening 136 as the sealing pad 126 absorbs fluids.

Figure 9:
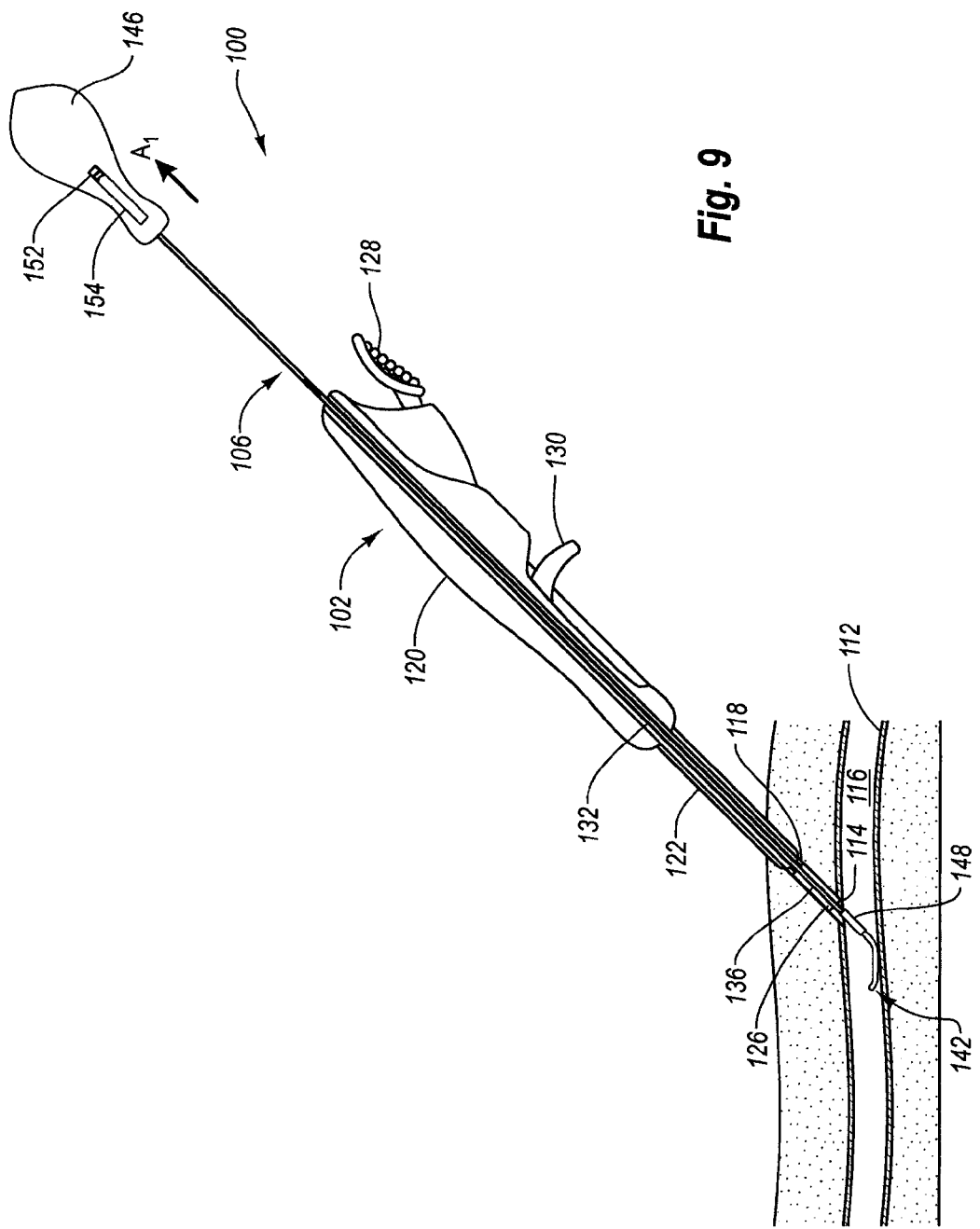
FIG. 9 is a side view of the guidewire FIG. 8 being operated to collapse the anchor of the guidewire.

Referring now to FIG. 9, the wire actuator 152 may be actuated within the actuator slot 154 to return the anchor 148 to an unexpanded or collapsed state. The anchor 148 in the unexpanded state may be sized to permit withdrawing of the locator wire assembly 106 proximally through the sealing pad 126 and sealing pad delivery device 102. Prior to withdrawing the locator wire assembly 106 relative to the sealing pad delivery device 102, the wire locking member 128 may be released to permit such relative axial movement. With the locator wire assembly 106 removed from the sealing pad 126, the sealing pad 126 may continue to absorb fluids and expand within the percutaneous incision to provide improved sealing and closure of the vessel puncture 114 and percutaneous incision 118.

Figure 10:
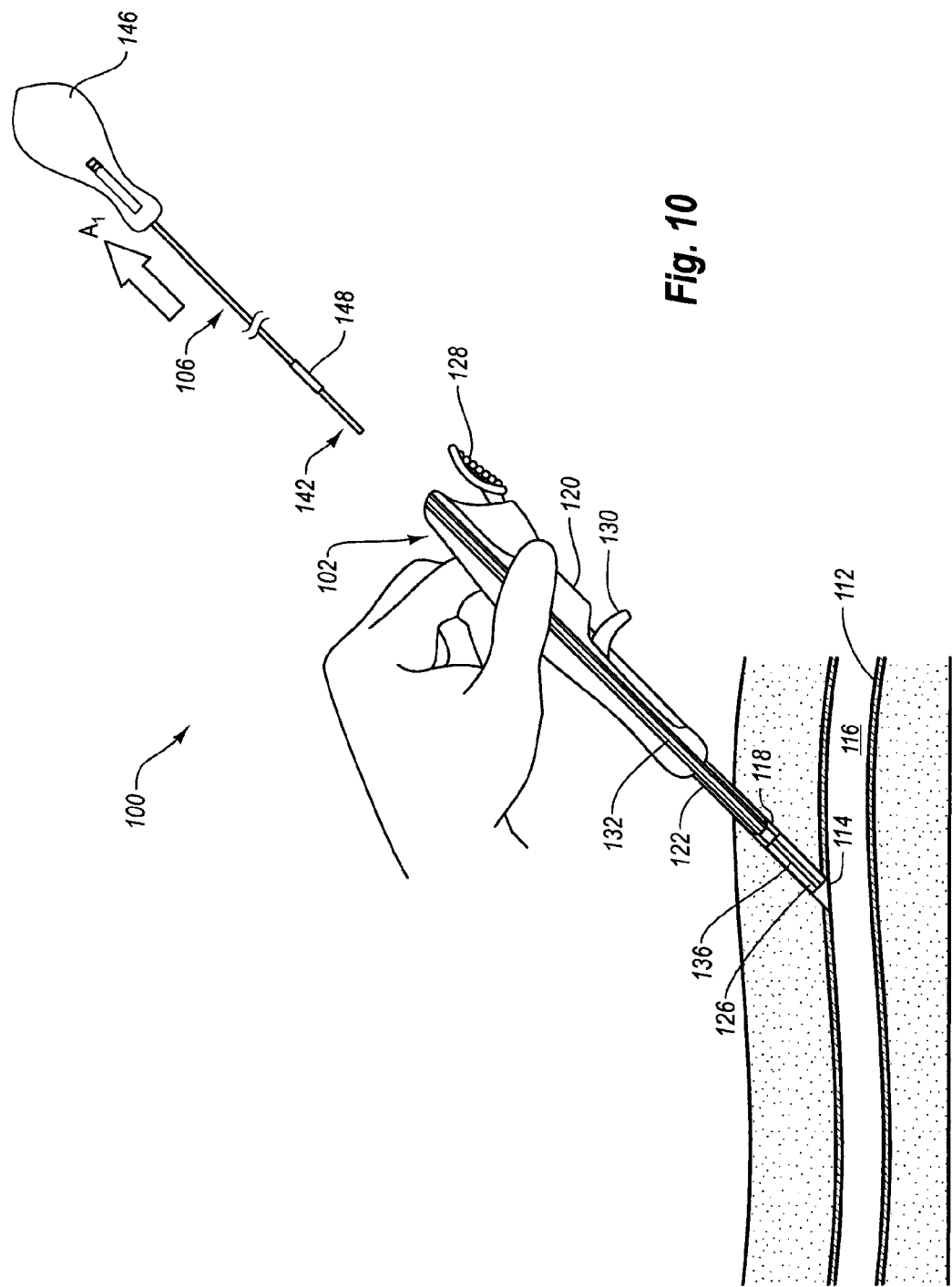
FIG. 10 is a side view of the guidewire FIG. 9 being withdrawn out of the closure device.

The sealing pad delivery device 102 may be retained in a fixed axial position relative to the sealing pad 126 during withdrawal of the locator wire assembly 106 as shown in FIG. 10 to help maintain the sealing pad 126 within the percutaneous incision 118. The locator wire assembly 106 may be completely withdrawn out of the sealing pad delivery device 102 as shown in FIG. 10 prior to withdrawing the sealing pad delivery device 102 out of the percutaneous incision 118. Alternatively, the locator wire assembly 106 may be withdrawn proximally out of the sealing pad 126 while being at least partially retained within the sealing pad delivery device 102. Subsequently, the sealing pad delivery device 102 and locator wire assembly 106 may be withdrawn together out of the percutaneous incision 118.

In an alternative method step, the locator wire assembly 106 may be maintained in the position shown in FIGS. 8 and 9 after the sealing pad 126 has been exposed within the percutaneous incision 118 and while the sealing pad delivery device 102 is withdrawn out of the percutaneous incision 118. The locator wire assembly 106 may then be withdrawn proximally out through the sealing pad 126 and percutaneous incision 118 with the sealing pad delivery device 102 still maintained mounted to the locator wire assembly 106. Alternatively, the sealing pad delivery device 102 may be dismounted from the locator wire assembly 106 (i.e., in the lateral or radial direction) while the locator wire assembly 106 remains at least partially inserted through the percutaneous incision 118.

Figure 11:
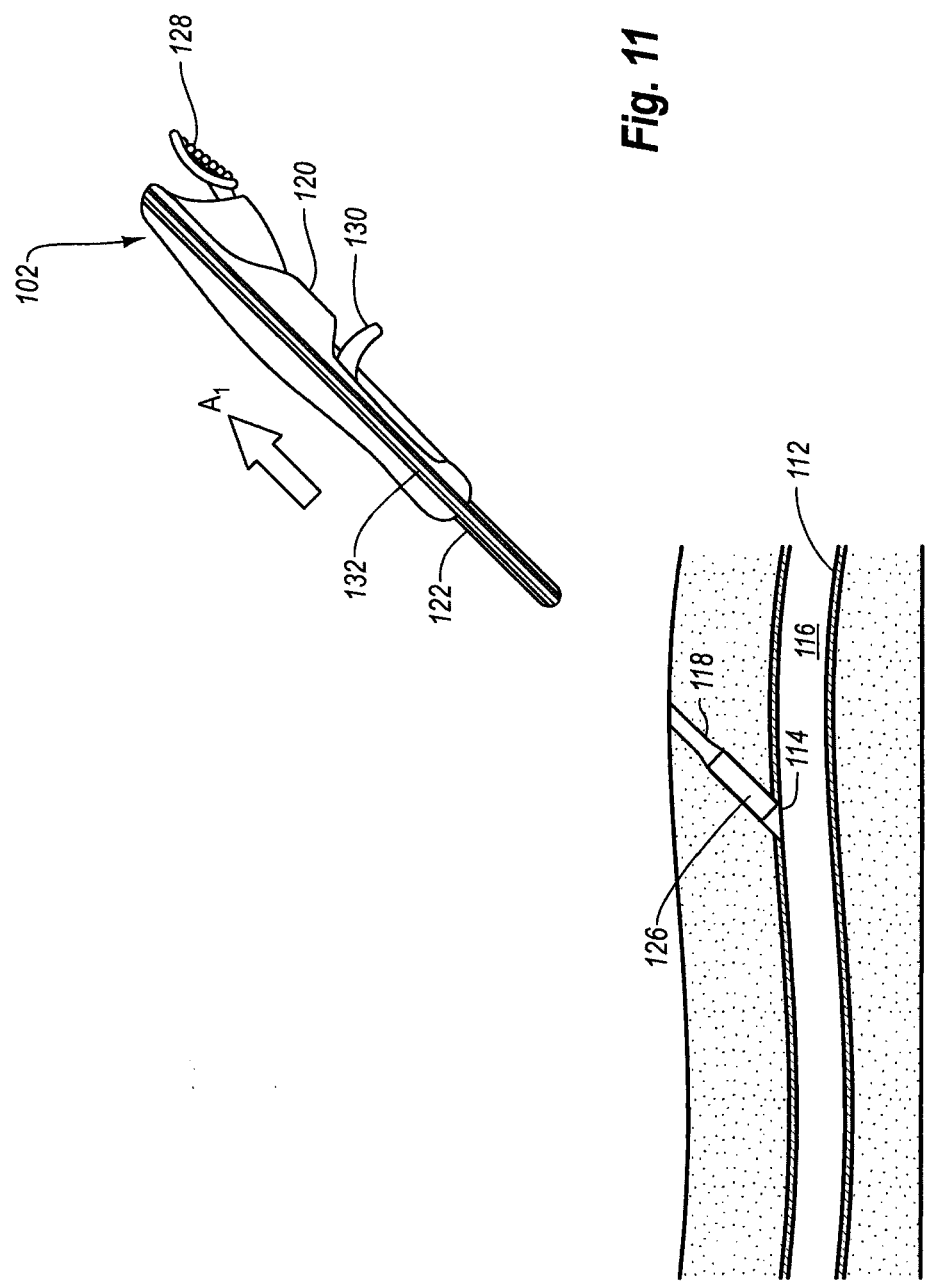
FIG. 11 is a side view of the closure device of FIG. 10 being withdrawn out of the percutaneous incision.

FIG. 11 illustrates the sealing pad delivery device 102 withdrawn out of the percutaneous incision 118 after the sealing pad 126 has been disposed within the percutaneous incision 118 and after the locator wire assembly 106 has been withdrawn out of the sealing pad 126 and percutaneous incision 118.

Many types of anchor structures may be used with the locator wire assemblies described herein. In at least one example, the anchor comprises an expandable basket or cage-type structure that is covered with, for example, a flexible membrane. A wire actuator that extends along at least a portion of the length of the locator wire assembly is used to expand and contract the basket or cage structure within the membrane. Other anchor constructions and actuator arrangements are possible for use in the locator wire assemblies described herein. In one example, an inflation balloon is used instead of a mechanically actuated anchor member. In other examples, the guidewire does not include an anchor member, but does include a handle for improved ease in handling the guidewire.

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:
1. A tissue puncture closure assembly, comprising:
  a wire assembly including:
    a proximal end portion and a distal end portion;
    a temporary expandable anchor positioned at the distal end portion, the temporary expandable anchor having a collapsed state and an expanded state;
  a sealing pad delivery device including:
    a carrier tube;
    a sealing pad positioned in the carrier tube;
    a lateral wire slot defined in an outer surface of the sealing pad delivery device and extending along at least a portion of respective lengths of the sealing pad delivery device, the carrier tube, and the sealing pad, the lateral wire slot being configured to permit mounting of the sealing pad delivery device to the wire assembly in a lateral direction;
    a wire locking member configured to releasably lock axial movement of the sealing pad delivery device relative to the wire assembly, the wire assembly being laterally movable relative to the wire locking member when the sealing pad delivery device is mounted to the wire assembly in a lateral direction;
    wherein the anchor in the collapsed state is proximally withdrawable through the sealing pad of the sealing pad delivery device.
2. The tissue puncture closure assembly of claim 1, wherein the lateral wire slot is configured to provide a snap-fit connection of the sealing pad delivery device to the wire assembly.

3. The tissue puncture locator device of claim 1, wherein the sealing pad delivery device further includes a housing, and the lateral wire slot is defined in an outer surface of the housing.

4. The tissue puncture locator device of claim 1, wherein the wire assembly further includes a handle positioned at the proximal end portion and an anchor actuator mounted to the handle.

5. The tissue puncture locator device of claim 1, wherein the wire assembly includes a tubular portion defining a lumen, and a wire member positioned in the lumen, wherein relative movement between the tubular portion and the wire member expands and contracts the anchor.

6. The tissue puncture locator device of claim 5, wherein the wire assembly further includes an anchor actuator positioned at the proximal end portion and configured to move the wire member relative to the tubular portion.

7. The tissue puncture locator device of claim 6, wherein the sealing pad delivery device includes a wire lumen sized to receive a portion of the wire assembly that is located between the distal and proximal end portions, and the proximal end portion of the wire assembly is sized greater than the wire lumen.

8. A tissue puncture closure device adapted for insertion into and sealing of a tissue puncture in a tissue wall, the closure device comprising:
   a housing;
   a carrier tube extending from the housing, the carrier tube having a carrier tube lateral slot;
   a sealing pad positioned in the carrier tube, the sealing pad having a sealing pad lateral slot being aligned with the carrier tube lateral slot;
   a guidewire lumen extending through the housing and carrier tube;
   wherein the closure device is operable to mount to a guidewire that is positioned in the tissue puncture by inserting the guidewire through the lateral slots of the carrier tube and the sealing pad and into the guidewire lumen;
   a wire locking member configured to fix axial movement of the closure device relative to the guidewire, the guidewire moving laterally relative to the wire locking, member when inserted into the guidewire lumen.

9. The tissue puncture closure device of claim 8, wherein a portion of the guidewire located between proximal and distal ends of the guidewire is inserted into the lateral guidewire slot.

10. The tissue puncture closure device of claim 8, further comprising an tube retractor actuator operable to withdraw the carrier tube relative to the housing to expose the sealing pad.

11. The tissue puncture closure device of claim 10, wherein the lateral guidewire slot includes a tapered construction.

12. The tissue puncture closure device of claim 11, wherein the lateral guidewire slot is configured to provide a snap-fit connection between the guidewire and the closure device.

\* \* \* \* \*